United States Patent [19]
Narayanan et al.

[11] Patent Number: 6,033,681
[45] Date of Patent: Mar. 7, 2000

[54] EMULSION CONCENTRATES OF FUNGICIDES, AND AQUEOUS USE FORMULATIONS THEREOF FOR WOOD PRESERVATION

[75] Inventors: Kolazi S. Narayanan, Wayne, N.J.; Domingo Jon, New York, N.Y.; Donald Prettypaul, Englewood, N.J.

[73] Assignee: ISP Investments Inc., Wilmington, Del.

[21] Appl. No.: 09/139,810

[22] Filed: Aug. 25, 1998

[51] Int. Cl.⁷ .......................... A01N 25/00; A01N 25/24; A01N 25/08; A01N 43/50
[52] U.S. Cl. .......................... 424/405; 424/407; 424/409; 514/399
[58] Field of Search ...................................... 424/405, 407, 424/409; 514/255, 481, 399

[56] References Cited

U.S. PATENT DOCUMENTS

| | | | |
|---|---|---|---|
| 5,354,726 | 10/1994 | Narayanan et al. | 504/116 |
| 5,672,353 | 9/1997 | Narayanan | 424/409 |
| 5,766,615 | 6/1998 | Narayanan | 424/405 |

*Primary Examiner*—S. Mark Clardy
*Assistant Examiner*—Alton Pryor
*Attorney, Agent, or Firm*—Walter Katz; William J. Davis; Marilyn J. Maue

[57] ABSTRACT

What is described herein are matrices, emulsion concentrates and aqueous use formulations of fungicides, effective for wood preservation applications, having increased penetration and rainfastness properties.

8 Claims, No Drawings

EMULSION CONCENTRATES OF FUNGICIDES, AND AQUEOUS USE FORMULATIONS THEREOF FOR WOOD PRESERVATION

BACKGROUND OF THE INVENTION

1. Field of the Invention

This invention relates to systems for delivery of fungicides, and, more particularly, to emulsifiable concentrates and aqueous use formulations thereof for wood coating applications.

2. Description of the Prior Art

Formulations for wood preservation which contain fungicides and other protective components are used in the presence of water under immersion conditions. However, it is found that these protective agents are washed off under these adverse water conditions. Accordingly, it is an object of this invention to provide compositions containing active fungicides which exhibit increased penetration and rainfastness characteristics.

SUMMARY AND DESCRIPTION OF THE INVENTION

The components used herein are listed in Table 1 below:

TABLE 1

| | |
|---|---|
| Agsol® EX 1 = | N-Methylpyrrolidone, NMP, International Specialty Products (ISP) |
| Agsol® EX 8 = | N-Octylpyrrolidone, NOP, (ISP) |
| Pluronic® L31 = | EO/PO Block Copolymer, (BASF) |
| Alkamuls® EL 620 = | Ethoxylated Castor Oil, 30 EO, (Rhone-Poulenc) |
| Alkamuls® EL 719 = | Ethoxylated Castor Oil, 40EO, (Rhone-Poulenc) |
| Agrimer® AL 25 = | C16 Alkylated vinylpyrrolidone copolymer, (ISP) |
| Agrimax® 3H = | a mixture of alkylpyrrolidone, oil, surfactants and water insoluble polymers - (ISP)* |
| | (2-Thiocyanomethyl-thio)benzothiazole) - (TCMTB) |

*commercial product

The emulsifiable concentrates of the invention are given in Table 2 below:

TABLE 2

| Emulsifiable Concentrate (% by Wt.) | | |
|---|---|---|
| | | Suitable |
| Fungicide | | |
| Preferred | | |
| TCMTB (active) | 5–20 | 7–15 |
| Emulsifiers | | |
| Alkamuls EL 620 | 30–80 | 45–65 |
| Pluronic L31 | 0–30 | 5–15 |
| or | | |
| Agrimax 3H | 60–90 | 75–85 |
| Alkamuls EL 719 | 0–30 | 5–20 |
| Solvent | | |
| NMP | 5–50 | 15–30 |
| NOP | 0–30 | 5–15 |
| Polymer | | |
| Agrimer AL 25 | 0–30 | 5–15 |

In the absence of the active fungicide, a matrix composition is provided, for example, Matrix-1 is given in Table 3 below:

TABLE 3

| Matrix 1 | |
|---|---|
| Alkamuls® EL 620 | 58.4% |
| Pluronic® L 31 | 9.7% |
| Agsol® EX 1 | 22.2% |
| Agsol® EX 8 | 9.7% |
| 100% | |

The invention will be described hereinafter with reference to the following examples.

EXAMPLE 1

An emulsifiable concentrate was prepared by mixing 10 g of TCMTB in 85.72 g of Matrix 1. The mixture was stirred on a wheel for 10 minutes. The concentrate obtained was clear, homogeneous low viscosity formulation, which was stable over a temperature range of 5° C. to 45° C. during a period of 21 days.

The emulsion concentrate then was diluted with water at a ratio of 1:20 with 1000 ppm hard water expressed as $CaCO_3$ equivalent to produce an aqueous formulation containing 0.5% TCMTB; it had a particle size of less than 0.13 microns, determined at a 90% population. The aqueous pour-on formulation remained stable for greater than 21 days when kept at both 15° C. and 35° C.

EXAMPLE 2

Example 1 was repeated with the addition of 10 g of Agrimer AL-25 to Matrix 1. Similar performance results were observed as in Example 1.

EXAMPLE 3

An emulsifiable concentrate was prepared by mixing 10 g of TCMTB in 8.57 g of Alkamuls EL 719 and 7.15 g of Agrimax 3H. Similar results were obtained.

EXAMPLE 4

Example 1 was repeated with 15 g of TCMTB. Similar results were obtained.

EXAMPLE 5

An emulsifiable concentrate was prepared by mixing 15 g of TCMTB in 78.5 g of a preconcentrate of 68.9 g of Matrix 1 and 7.6 g of Agrimer AL-25. Similar results were obtained.

EXAMPLE 6

An emulsifiable concentrate was prepared by mixing 15 g of TCMTB in 85 g of a preconcentrate of 76.5 g of Agrimax 3H and 8.5 g of Alkamuls EL 719. Similar results were obtained.

EXAMPLE 7

An emulsifiable concentrate was prepared by mixing 10 g of TCMTB in 85.7 g of a preconcentrate of 83.7 g of Matrix 1 and 2 g of Agrimer AL-25. The emulsion concentrate was diluted with water at a ratio of 1:2. The diluted sample containing 5% TCMTB remained stable and clear for a time interval greater than 14 days at room temperature.

EXAMPLE 8

An emulsifiable concentrate was prepared by mixing 10 g of TCMTB in 85.72 g of Matrix 1. The mixture was stirred on a wheel for 10 minutes. The emulsion concentrate was diluted at the ratio of 1:33 in water to produce an aqueous formulation containing 0.3% TCMTB. 35 pieces of timber "Pine Ellliotis" (a common white wood, 50×10×2.5 each) was dipped in a 30 liter bath solution for 30 seconds. The pieces were stocked and left in the open for 35 days and wetted uniformly during dry periods. After this period, each piece was qualified using a 0–10 scale depending on the amount of fungus in the timber (10 points: no fungus at all). The calculated average and standard deviation values were 8.1 and 2.0, respectively. The result was equivalent to a commercial product containing 0.5% TCMTB. The calculated average value and standard deviation of this commercial product was 8.9 and 1.3, respectively.

EXAMPLE 9

Example 8 was repeated with the addition of 10 g of Agrimer AL-25 to Matrix 1. The calculated average result was 8.5 with the standard deviation of 1.5. For comparison purposes, the calculated value of a blank set that was also treated by dipping 35 pieces of timber in 30 liters of water was 0.8, with the average deviation of 1.4.

EXAMPLE 10

An emulsifiable concentrate was prepared by mixing 10 g of TCMTB in 85.72 g of a matrix of 76.5 g of Agrimax® 3H and 8.5 g of Alkamuls® EL 719. The mixture was stirred on a wheel for 10 minutes. The emulsion concentrate was diluted at the ratio of 1:33 in water to produce an aqueous formulation containing 0.3% TCMTB. 35 pieces of timber "Pine Ellliotis" (a common white wood, 50×10×2.5 each) was dipped in a 30 liter bath for 30 seconds. The pieces were stocked and left in the open for 35 days and wetted uniformly during dry periods. After this period, each piece was qualified using a 0–10 scale depending on the amount of fungus the timber had (10 points: no fungus at all). The calculated average and standard deviation values were 8.4 and 1.3, respectively. The result was equivalent to a commercial product containing 0.3% TCMTB. The calculated average value and standard deviation of this commercial product was 8.5 and 1.2, respectively.

While the invention has been described with particular reference to certain embodiments thereof, it will be understood that changes and modifications may be made which are within the skill of the art. Accordingly, it is intended to be bound only by the following claims, in which:

What is claimed is:

1. An emulsifiable concentrate of a fungicide useful for wood preservation comprising, by weight,
    (a) 7–15% of a fungicide,
    (b) 45–65% of an ethoxylated castor oil (30 EO),
    (c) 5–15% of an EO/PO block copolymer,
    (d) 5–15% of a $C_{16}$ alkylated vinyl pyrrolidone copolymer,
    (e) 15–30% of N-methyl pyrrolidone, and
    (f) 5–15% of N-octyl pyrrolidone.

2. A concentrate according to claim 1 wherein said fungicide is 2-(thiocyanomethylthio) benzothiazole.

3. A matrix concentrate according to claim 1 wherein (a) is absent.

4. An emulsifiable concentrate comprising, by weight,
    (a) 7–15% of a fungicide,
    (b) 75–85% of a mixture of alkyl pyrrolidone, oil, surfactants and water-insoluble polymers,
    (c) 5–20% of an ethoxylated castor oil (40 EO),
    (d) 5–15% of a $C_{16}$ alkylated vinyl pyrrolidone copolymer,
    (e) 15–30% of N-methyl pyrrolidone, and
    (f) 5–15% of N-octyl pyrrolidone.

5. A concentrate according to claim 4 wherein said fungicide is 2-(thiocyanomethylthio) benzothiazole.

6. A matrix concentrate according to claim 4 wherein (a) is absent.

7. An aqueous formulation for wood preservation exhibiting increased wood penetration and rainfastness comprising the emulsion concentrate of claim 1 or 4 and water.

8. A formulation according to claim 7 wherein the fungicide is 2-(thiocyanomethylthio) benzothiazole.

* * * * *